(12) United States Patent
Mas et al.

(10) Patent No.: US 8,580,712 B2
(45) Date of Patent: Nov. 12, 2013

(54) BIS(DIALKYLAMIDE) COMPOUNDS AND DIVERSE APPLICATIONS THEREOF

(75) Inventors: Jean-Manuel Mas, Shainghai (CN); Valerio Bramati, Arese (IT); Massimo Guglieri, Paris (FR); Wagner Celio Ferraz Lourenco, Sao-Paulo (BR)

(73) Assignee: Rhodia Operations, Aubervilliers (FR)

( * ) Notice: Subject to any disclaimer, the term of this patent is extended or adjusted under 35 U.S.C. 154(b) by 689 days.

(21) Appl. No.: 12/520,425

(22) PCT Filed: Dec. 19, 2007

(86) PCT No.: PCT/EP2007/064235
§ 371 (c)(1),
(2), (4) Date: Dec. 28, 2009

(87) PCT Pub. No.: WO2008/074837
PCT Pub. Date: Jun. 26, 2008

(65) Prior Publication Data
US 2010/0113279 A1 May 6, 2010

(30) Foreign Application Priority Data
Dec. 19, 2006 (FR) .................................. 06 11060

(51) Int. Cl.
*A01N 25/02* (2006.01)
*B01F 1/00* (2006.01)
*C07C 233/56* (2006.01)

(52) U.S. Cl.
USPC ........................... 504/362; 564/160; 252/364

(58) Field of Classification Search
USPC ........................... 564/160; 504/362; 252/364
See application file for complete search history.

(56) References Cited

U.S. PATENT DOCUMENTS

| 3,288,794 A | 11/1966 | Kuceski |
| 5,206,225 A | 4/1993 | Horstmann et al. |
| 2005/0003312 A1 | 1/2005 | Mura et al. |

FOREIGN PATENT DOCUMENTS

| DE | 3339386 | * | 5/1985 |
| EP | 143303 | * | 6/1985 |
| EP | 0453899 B1 | | 10/1991 |
| JP | 46-33014 | * | 9/1971 |
| JP | 02 006124649 | * | 5/2006 |
| JP | 2006-124649 | | 5/2006 |

OTHER PUBLICATIONS

EP 143303(English abstract), 1985.*
JP 46033014(English abstract), 1971.*
RN 100071-13-4, 1985.*
Kim et al, Macromolecular Raid Comm., 2005, 26, 1499-1503.*
Giannella et al., "Molecular Requirements of the Active Sites of the Cholinergic Receptors, XII 3-Methyl-2-oxo-1-dimethylaminomethylcyclopentane methiodide as a new selective agonist for the nicotinic receptor," Farmaco, Edizione Scientifica, Societa Chimica Italiana, Pavia, IT, 1980, vol. 35, No. 4, pp. 253-262.
Gajewski et al., "Variable Transition State Structure in 3,3-Sigmatropic Shifts from α-Secondary Deutorium Isotope Effects," JACS, American Chemical Society, Washington, DC, US, vol. 101, No. 22, 1979, pp. 6693-6704.
Database Casreact, Chemical Abstracts Service, Columbus, Ohio, US, an 89:129083; 1989, abstract of Malkhasyan et al. "Doklady Akadem" Nauk Armyans KOL SSR (1978), 66(3), 156-159, abstract.
Kim et al., "Living Polymerization of N,N-Diphenylacrylamide with Triisobutylaluminum", Macromolecular: Rapid Communications, Wiley-VCH Verlag, Weinheim, DE, vol. 26, No. 18, 2005, pp. 1499-1503.
International Search Report for corresponding PCT/EP2007/064235, dated Mar. 28, 2008, in French and English, 8 pages.

* cited by examiner

Primary Examiner — Shailendra Kumar
(74) Attorney, Agent, or Firm — Dentons US LLP

(57) ABSTRACT

Novel bis(dialkylamide) compounds having the formula:

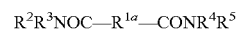

are particularly useful solvents, for example in plant-protection formulations.

14 Claims, No Drawings

BIS(DIALKYLAMIDE) COMPOUNDS AND DIVERSE APPLICATIONS THEREOF

CROSS-REFERENCE TO PRIORITY/PCT APPLICATIONS

This application is a national phase of PCT/EP 2007/064235, filed Dec. 19, 2007 and designating the United States (published in the French language on Jun. 26, 2008, as WO 2008/074837 A1; the title and abstract were also published in English), and claims foreign priority under 35 U.S.C. §119 of FR 0611060, filed Dec. 19, 2006, each hereby expressly incorporated by reference in its entirety and each assigned to the assignee hereof.

A subject matter of the present invention is novel bis(dialkylamide) compounds, uses of these compounds and at least one preparation process. These compounds can be used in particular as solvents, for example in plant-protection formulations.

Industry uses numerous chemical compounds as solvents, for example for preparing chemicals and materials, for formulating chemical compounds or for treating surfaces. For example, solvents are used for the formulation of plant-protection active principles, in particular in the form of emulsifiable concentrates (EC) intended to be diluted in water by the farmer, before application to a field.

Industry is on the lookout for novel compounds which make it possible to vary or to optimize products and processes in which solvents, in particular polar solvents, are to be used. Industry needs in particular compounds of modest cost exhibiting advantageous operational properties. Industry also needs compounds exhibiting a toxicological and/or ecological profile perceived as favorable, in particular a low volatility (low content of VOCs), a good biodegradability, a low toxicity and/or a low level of danger.

The use of dialkylamides as solvents is known. These concern a product of formula R—CONMe$_2$ where R is a hydrocarbon group, such as an alkyl, typically with 6 to 30 carbon atoms. Such products are sold in particular under the name Genagen® by Clariant. These solvents have applications in particular in the plant-protection field.

Diesters of dicarboxylic acids are also known as solvents, in particular the diesters obtained by esterification of a mixture of adipic acid, glutaric acid and succinic acid. Such products are sold in particular under the names Rhodiasolv® RPDE and Rhodiasolv® DIB by Rhodia.

The document U.S. Pat. No. 3,288,794 describes bis(dialkylamide)s of linear dicarboxylic acids of formula HOOC—(CH$_2$)$_z$—COOH such as adipic acid (z=4), glutaric acid (z=3) or succinic acid (z=2). These products are solids; the melting points are of the order of 80° C. They thus cannot be used as solvents at more modest temperatures, in particular at ambient temperature.

The document EP 186 950 describes bis(amide)s of dicarboxylic acids obtained from a monoamide, CO and an amine. This document describes in particular the preparation of adipamide of formula H$_2$NOC—(CH$_2$)$_z$—CONH$_2$ where z=4. The document teaches the use of the compounds as monomers or intermediates intended for the preparation of polymers.

The document U.S. Pat. No. 4,588,833 describes the preparation of substituted succinic acid amides. This document describes in particular the preparation of compounds of XOC—CH$_2$—CHR$^6$—CONEt$_2$ type where R$^6$ is a methyl or an ethyl. The products are prepared by bringing together CO, an alcohol or an amine HX, and crotonic acid dialkylamide or pent-3-enoic acid diethylamide. The document teaches the use of the compounds as antioxidants, as stabilizers for plastics or as intermediates in organic synthesis.

There remains a need, as explained above, for other compounds which can be of use in particular as solvents.

The invention meets this need by providing a compound of following formula (Ia):

$$R^2R^3NOC—R^{1a}—CONR^4R^5 \quad (Ia)$$

where R$^2$, R$^3$, R$^4$ and R$^5$, which are identical or different, are:
linear or branched or cyclic C$_1$-C$_6$, preferably C$_1$-C$_4$, alkyl groups or
phenyl groups,
characterized in that:
R$^{1a}$ is a divalent group of formula (IIa):

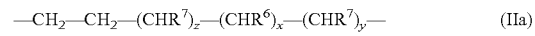
$$—CH_2—CH_2—(CHR^7)_z—(CHR^6)_x—(CHR^7)_y— \quad (IIa)$$

where:
x is an integer greater than 0,
y is a mean integer greater than or equal to 0,
z is a mean integer greater than or equal to 0,
R$^6$, which is identical or different, is a C$_1$-C$_6$, preferably C$_1$-C$_4$, alkyl group, and
R$^7$, which is identical or different, is a hydrogen atom or a C$_1$-C$_6$, preferably C$_1$-C$_4$, alkyl group.

Another subject matter of the invention is a process for the preparation of the compound of the invention.

Another subject matter of the invention is the use of the compound of the invention in formulations. Another subject matter of the invention is a process for the preparation of the formulations by addition of the compound of the invention. Another subject matter of the invention is formulations comprising the compound of the invention. The formulations can in particular be plant-protection formulations.

Another subject matter of the invention is the use of the compound as solvent, cosolvent and/or crystallization inhibitor. Another subject matter of the invention is a method of solvating, cosolvating and/or inhibiting crystallization by addition of the compound of the invention.

Compound of the Invention

The compound of the invention has the following formula (Ia):

$$R^2R^3NOC—R^{1a}—CONR^4R^5 \quad (Ia)$$

where R$^2$, R$^3$, R$^4$ and R$^5$, which are identical or different, are linear or branched C$_1$-C$_6$, preferably C$_1$-C$_4$, alkyl groups, characterized in that:
R$^{1a}$ is a divalent group of formula (IIa):

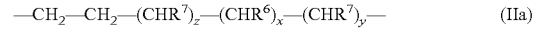
$$—CH_2—CH_2—(CHR^7)_z—(CHR^6)_x—(CHR^7)_y— \quad (IIa)$$

where:
x is an integer greater than 0,
y is a mean integer greater than or equal to 0,
z is a mean integer greater than or equal to 0,
R$^6$, which is identical or different, is a C$_1$-C$_6$, preferably C$_1$-C$_4$, alkyl group, and
R$^7$, which is identical or different, is a hydrogen atom or a C$_1$-C$_6$, preferably C$_1$-C$_4$, alkyl group.

The R$^2$, R$^3$, R$^4$ and R$^5$ groups, which are identical or different, are preferably chosen from the methyl, ethyl, propyl (n-propyl), isopropyl, n-butyl, isobutyl, n-pentyl, amyl, isoamyl, hexyl or cyclohexyl groups. They are preferably identical.

The R$^7$ groups can in particular be linear, branched or cyclic.

According to a specific form, the R$^{1a}$ group is preferably a group such that y=z=0.

The $R^{1a}$ group is preferably a group such that:
x=1,
y=z=0,
$R^6$=methyl.

Such an $R^{1a}$ group is such that the compound of formula HOOC—$R^{1a}$—COON is 2-methylglutaric acid.

Preferably, for the compound:
the $R^{1a}$ group is such that:
x=1,
y=z=0,
$R^6$=methyl, and
$R^2$, $R^3$, $R^4$ and $R^5$ are identical and chosen from the methyl, ethyl, n-propyl or isobutyl groups.

Examples of compounds are the compounds of following formula:

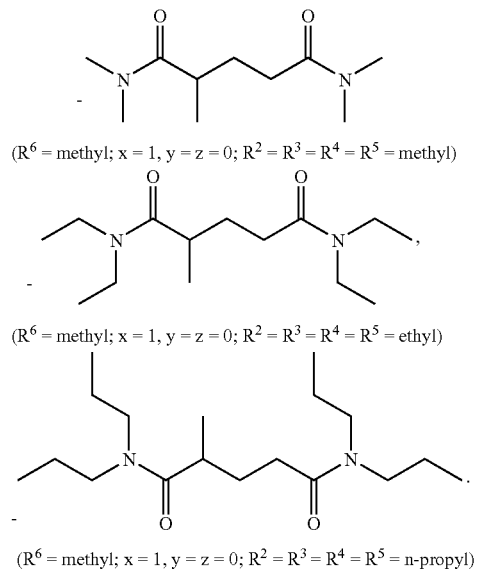

($R^6$ = methyl; x = 1, y = z = 0; $R^2$ = $R^3$ = $R^4$ = $R^5$ = methyl)

($R^6$ = methyl; x = 1, y = z = 0; $R^2$ = $R^3$ = $R^4$ = $R^5$ = ethyl)

($R^6$ = methyl; x = 1, y = z = 0; $R^2$ = $R^3$ = $R^4$ = $R^5$ = n-propyl)

The compound can in particular be an amidation or transamidation product. It can in particular be included in a mixture of compounds, for example in a reaction product comprising several different compounds.

The compound of the invention advantageously exhibits a melting point of less than or equal to 25° C.

It is mentioned that the compound is typically other than a compound of formula (phenyl)$_2$-NOC—CH$_2$—CH$_2$—CH(CH$_3$)—CON-(phenyl)$_2$.

Material Composition Comprising the Compound of the Invention

The compound of the invention can be included in a material composition. Material composition is understood to mean a more or less complex composition comprising several chemical compounds. It can typically be an unpurified or partially purified reaction product. The compound of the invention can in particular be isolated and/or sold and/or used in the form of a material composition comprising it.

In the material composition, the compound of the invention can represent at least 10% by weight. Preferably, it is the main compound of the material composition. Main compound is understood to mean, in the present patent application, the compound having the highest content, even if its content is less than 50% by weight (for example, in a mixture of 40% of A, 30% of B and 30% of C, the product A is the main compound). More preferably still, the compound of the invention represents at least 50% by weight of the material composition, for example from 70 to 95% by weight and even from 75 to 90% by weight.

As indicated above, the material composition can be a reaction product, in particular an amidation or transamidation product.

The material composition can in particular comprise, in addition to the compound of the invention, a product of following formula (Ib):

$$R^2R^3NOC—R^{1b}—CONR^4R^5 \quad (Ib)$$

where:
$R^2$, $R^3$, $R^4$ and $R^5$, which are identical or different, are as defined above,
$R^{1b}$ is a divalent group of formula (IIb):

$$—CH_2—(CHR^7)_z—(CHR^6)_x—(CHR^7)_y— \quad (IIb)$$

where:
x is an integer greater than 0,
y is a mean integer greater than or equal to 0,
z is a mean integer greater than or equal to 0,
$R^6$, which is identical or different, is a $C_1$-$C_6$, preferably $C_1$-$C_4$, alkyl group, and
$R^7$, which is identical or different, is a hydrogen atom or a $C_1$-$C_6$, preferably $C_1$-$C_4$, alkyl group.

The $R^{1b}$ group is preferably a group such that:
x=1,
y=z=0,
$R^6$=ethyl.

Such an $R^{1b}$ group is such that the compound of formula HOOC—$R^{1b}$—COOH is 2-ethylsuccinic acid.

The material composition can in particular comprise, in addition to the compound of the invention, a product of following formula (Ic):

$$R^2R^3NOC—(CH_2)_w—CONR^4R^5 \quad (Ic)$$

where:
$R^2$, $R^3$, $R^4$ and $R^5$, which are identical or different, are as defined above, and
w is an integer greater than 0, preferably equal to 4.

When w=4, the product of formula HOOC—(CH$_2$)$_4$—COOH is adipic acid.

The material composition is in particular be a product of the amidation or transamidation of a mixture of methylglutaric acid, ethylsuccinic acid and optionally adipic acid, or of a diester of this mixture. In this case, the composition will comprise a mixture comprising:
the compound of the invention in which $R^{1a}$ is such that the compound of formula HOOC—$R^{1a}$—COOH is 2-methyl-glutaric acid,
the product of formula (Ib) in which $R^{1b}$ is such that the compound of formula HOOC—$R^{1b}$—COOH is 2-ethylsuccinic acid, and
optionally the product of formula (Ic) in which w=4.

The content of product of formula (Ib) in the material composition can, for example, be from 5 to 30% by weight or even from 5 to 20% by weight.

The content of product of formula (Ic) in the material composition can, for example, be zero or less that 15% or even less than 10%.

It is not ruled out for the material composition to comprise products other than those identified above. They can in particular be entities not converted to amides or different amide products from the compounds of the invention and products, for example diamides of adipic acid of formula ($R^2R^3$NOC—(CH$_2$)$_4$—CONR$^4$R$^5$). They can also be partially amidated or transamidated products (where one of the acid or ester functional groups of the two available has been converted to an amide).

A material composition which is particularly useful and/or practical and/or simple to access comprises:

from 70 to 95% by weight of the compound of formula (Ia), preferably from 75 to 90% by weight, preferably from 79 to 86% by weight, preferably of the compound of formula

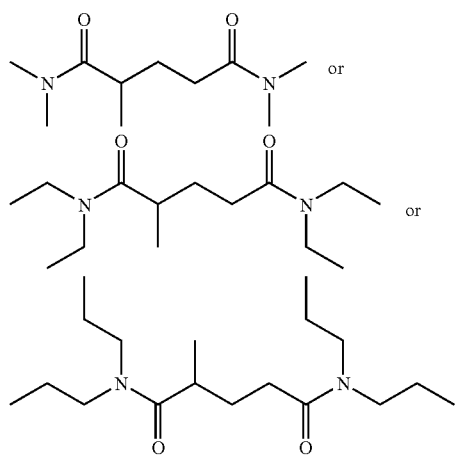

from 5 to 30% by weight of a compound of formula (Ib), preferably from 5 to 20% by weight, preferably from 7 to 12% by weight, preferably of N,N,N,N-tetramethyl-2-ethylsuccinamide or N,N,N,N-tetraethyl-2-ethylsuccinamide or N,N,N,N-tetra(n-propyl)-2-ethylsuccinamide, optionally, at most 15% by weight of a compound of formula (Ic), preferably at most 10% by weight, preferably at most 8% by weight, of another compound, for example from 2 to 7% by weight, preferably of N,N,N,N-tetramethyladipamide or N,N,N,N-tetraethyl-adipamide or N,N,N,N-tetra(n-propyl)adipamide.

The total of the percentages, with, if appropriate, other products which may be present, must be 100%.

The material composition advantageously exhibits a melting point of less than or equal to 25° C.

Process for the Preparation of the Compound or of the Material Composition

The compound of the invention can be prepared by any appropriate method. It will be preferable in particular to employ amidation or transamidation reactions on diacids or analogous diesters. Such reactions are known to a person skilled in the art. These methods can be carried out similarly for material compositions. It will be possible in particular to carry out amidation or transamidation reactions on mixtures of diacids or of analogous diesters.

Thus, a process for the preparation of a compound of the invention, if appropriate in a material composition, comprises a stage of amidation or trans-amidation by a compound of formula $R^2R^3NH$ and/or $HNR^4R^5$ of a compound of following formula (I'a):

$$R^8OOC-R^{1a}-COOR^8 \quad (I'a)$$

the compound of formula (I'a) being, if appropriate, as a mixture with a compound of following formula (I'b):

$$R^8OOC-R^{1b}-COOR^8 \quad (I'b)$$

and, if appropriate, as a mixture with a compound of following formula (I'c):

$$R^8OOC-(CH_2)_w-COOR^8 \quad (I'c)$$

where
$R^8$ is a hydrogen atom or a $C_1$-$C_6$ alkyl, preferably a methyl, and
$R^{1a}$ is as defined above,
$R^{1b}$ is as defined above, and
w is as defined above.

The compounds of formulae (I'a), (I'b) and (I'c) are regarded as diacids or analogous diesters respectively of the compound of the invention, of the product of formula (Ib) and of the product of formula (Ic).

The amidation or transamidation reaction can be carried out continuously, semicontinuously or batchwise. In order to improve the degree of conversion of the reaction (degree of conversion of the acid or diester) and/or to reduce the amount of unreacted product in a material composition and/or to increase the productive output, it is possible in particular to remove reaction by-products during the reaction. It is possible, for example, to remove, by evaporation (stripping), alcohols formed during a transamidation reaction. It should be noted that it is possible to use a very large excess of amine, an amine salt or any other means known to a person skilled in the art, for example described in the work "March's Advanced Organic Chemistry" by Michael B. Smith and Jerry March, 5th edition, John Wiley & Sons, pages 506-511.

The reaction can be followed by stages of filtration and/or of purification, for example by distillation.

It should be noted that the amidation or transamidation reaction can pass through activated intermediates, such as acid chlorides obtained, for example, from the compounds of formulae (I'a) and (I'b) by reaction with thionyl chloride. The separation of the hydrochloric acid, a by-product during this type of amidation reaction, from the reaction medium by any appropriate means (formation of salt, distillation) constitutes a driving force for shifting the reaction equilibrium towards the formation of the desired amide.

The diacids or diesters, in the form of mixtures in order to obtain a material composition, can be obtained in particular from a mixture of dinitrile compounds in particular produced in and recovered from the process for the manufacture of adiponitrile by double hydrocyanation of butadiene. This process, used on a large scale industrially to produce the great majority of the adiponitrile consumed worldwide, is described in numerous patents and books.

The reaction for the hydrocyanation of butadiene results predominantly in the formation of linear dinitriles but also in the formation of branched dinitriles, the two main ones of which are methyl-glutaronitrile and ethylsuccinonitrile.

The branched dinitrile compounds are separated by distillation in the stages for the separation and purification of adiponitrile and are recovered, for example, as top fraction in a distillation column.

The branched dinitriles can subsequently be converted to diacids or to diesters. One of the possible processes for the conversion of dinitriles to diesters corresponds to the use of the Pinner reaction, described in particular in French patent No. 1 488 857. Basically, this process consists in reacting the dinitrile compounds with an alcohol in the presence of a strong inorganic acid, such as sulfuric acid, and in then hydrolyzing the products obtained in order to recover diesters by distillation. This document also describes a specific embodiment of the process which consists in passing the mixture of dinitrile compounds and the alcohol through a bath of molten salts based on various alkali metal and ammonium sulfates, in order to avoid the formation of ammonium sulfate and to recover the ammonia by steam extraction.

Useful diesters can also be obtained by reaction between the dinitrile compounds, water and an alcohol in the gas phase and in the presence of a solid catalyst. The reaction temperature is advantageously greater than the condensation temperature of the diesters formed. Use may be made, as catalyst, of a solid acid catalyst, such as, for example, a silica gel, a silica/alumina mixture or supported boric or phosphoric acids. Use may also be made of macroporous aluminas, such as those described in the document EP 805 801.

The reaction temperature for the conversion of dinitriles to diesters can be between 200° C. and 450° C., preferably between 230° C. and 350° C. The reaction can be carried out under any pressure, advantageously of between 0.1 and 20 bar. At the outlet of the reactor, the vapors can be rapidly cooled to a temperature of less than or equal to 150° C. The ammonia, then the water and the excess alcohol can be separated by distillation from the mixture obtained.

Useful diesters can also be obtained by reaction between the dinitrile compounds and an inorganic base, in order to obtain acid salts, then neutralization of these salts with an acid, followed by an esterification with an alcohol. A useful process is described in detail in particular in the French patent application filed on 9 Jun. 2006 under No. 06 05119.

Useful diacids can be obtained by reaction between the dinitrile compounds and an inorganic base, in order to obtain acid salts, followed by neutralization of these salts with an acid. Useful diacids can also be obtained by acid hydrolysis of the dinitrile compounds.

Uses

The compound of the invention and/or a material composition comprising it described above can be used in particular as solvent, cosolvent and/or crystallization inhibitor, or as coalescence agent.

Cosolvent is understood to mean that other solvents can be combined with it. The use as solvent or cosolvent comprises in particular uses for dissolving a compound in a formulation or in a reaction medium, the use for completely or partially dissolving a product to be removed (degreasing, stripping) and/or the use for facilitating the detachment of films of materials. The product to be removed can in particular be an oil, greases, waxes, petroleum, resins, paint or graffiti. It can be used as pretreating agent which facilitates the deleting of graffiti after it has appeared.

The compound of the invention and/or a material composition comprising it described above can in particular be used, for the functions indicated above or for others, in a plant-protection formulation, in a cleaning formulation, in a stripping formulation, in a degreasing formulation, in a lubricating formulation, in a formulation for cleaning or degreasing textiles, in a coating formulation, for example in a paint formulation, in a pigment or ink formulation or in a plastic formulation.

The compound can, for example, be used as coalescence agent in a water-based paint formulation. It can be used as solvent in a non-water-based paint formulation.

The compound can in particular be used as degreasing agent on metal surfaces, for example surfaces of implements, manufactured items, metal sheets or molds, in particular made of steel or aluminum or of alloys of these metals.

The compound can in particular be used as cleaning solvent on hard surfaces or textile surfaces. It can be used for cleaning industrial sites, for example sites for the exploitation of oil or gas, for example oil platforms, which may or may not be offshore.

The compound can in particular be used as solvent for stripping paints or resins on surfaces of implements, for example casting molds, or on surfaces of industrial sites (floors, partitions, and the like).

The compound can in particular be of use as solvent for cleaning or stripping printing devices.

The cleaning and/or degreasing formulations can in particular be formulations for household care, carried out in homes or in public areas (hotels, offices, factories, and the like). They can be formulations for cleaning hard surfaces, such as floors, surfaces of kitchen and bathroom furniture and fittings, or dishes. These formulations can also be used in the industrial sphere for degreasing manufactured products and/or for cleaning them.

The compound of the invention and/or a material composition comprising it described above can in particular be used in plant-protection formulations comprising a solid active product. Further details are given below, where the word "solvent" can denote the compound of the invention or a material composition comprising it described above.

Detailed Use in the Context of Plant-Protection Formulations

The plant-protection formulation is generally a concentrated plant-protection formulation comprising an active compound.

Agriculture makes use of numerous active materials, such as fertilizers or pesticides, for example insecticides, herbicides or fungicides. The reference is to plant-protection active products (or active materials). Plant-protection active products are generally products in the pure or highly concentrated form. They have to be used on farms at low concentrations. To this end, they are generally formulated with other ingredients in order to make possible easy dilution in weight by the farmer. The reference is to plant-protection formulations. The dilution carried out by the farmer is generally carried out by mixing the plant-protection formulation with water.

Thus, plant-protection formulations have to make possible easy dilution in weight by the farmer in order to obtain a product in which the plant-protection product is correctly dispersed, for example in the solution, emulsion, suspension or suspoemulsion form. Plant-protection formulations thus make possible the transportation of a plant-protection product in the relatively concentrated form, easy packaging and/or easy handling for the final user. Different types of plant-protection formulations can be used according to the different plant-protection products. Mention is made, for example, of emulsifiable concentrates ("EC"), concentrated emulsions (Emulsion, oil in water, "EW"), microemulsions ("ME"), wettable powders ("WP") or water-dispersible granules ("WDG"). The formulations which it is possible to use depend on the physical form of the plant-protection product (for example solid or liquid) and on its physicochemical properties in the presence of other compounds, such as water or solvents. After dilution in weight by the farmer, for example by mixing with water, the plant-protection product can occur in different physical forms: solution, dispersion of solid particles, dispersion of droplets of the product, droplets of solvent in which the product is dissolved, and the like. Plant-protection formulations generally comprise compounds which make it possible to obtain these physical forms. They can, for example, be surfactants, solvents, inorganic supports and/or dispersants. Very often, these compounds do not have an active nature but a nature of intermediate of help to the formulation. Plant-protection formulations can in particular be in the liquid form or in the solid form.

In order to prepare plant-protection formulations of solid plant-protection active products, it is known to dissolve the product in a solvent. The plant-protection formulation thus comprises a solution of the product in the solvent. The formulation can be in the solid form, for example in the form of a wettable powder (WP) where the solution impregnates an inorganic support, for example kaolin and/or silica. The formulation can alternatively be in the liquid form, for example in the form of an emulsifiable concentrate (EC) exhibiting a single clear liquid phase comprising the solvent and the product in solution, which can form an emulsion by addition of water, without stirring or with gentle stirring. It can also be or in the form of a cloudy concentrated emulsion (EW), the phase of which dispersed in the water comprises the solvent and the product in solution in the solvent. It can also be in the form of a clear microemulsion (ME), the phase of which dispersed in the water comprises the solvent and the product in solution in the solvent.

Some solid plant-protection active principles are often difficult to formulate. For example, tebuconazole is a particularly effective and widely used fungicide, in particular for the cultivation of soya. For some plant-protection active principles, it is difficult to produce concentrated formulations which are easy to dilute for the farmer, which are stable and which are without substantial disadvantages (known or perceived) with regard to safety, toxicity and/or ecotoxicity. For some active principles, it is difficult to formulate at relatively high concentrations with a satisfactory stability. In particular, it is necessary to avoid the appearance of crystals, in particular at low temperature and/or during the dilution and/or during the storage at high temperature of the diluted composition. The crystals may have negative effects, in particular may block the filters of the devices used to spread the diluted composition, may block the spray devices, may reduce the overall activity of the formulation, may create needless problems of waste procedures in order to remove the crystals, and/or may cause poor distribution of the active product over the agricultural field.

The formulations comprising the solvent exhibit in particular:
- dissolution of large amounts of active principles,
- absence of crystallization, even under demanding conditions,
- good biological activity, which can be due to good solvation, and/or
- a safety, toxicology and/or ecotoxicology profile perceived as favorable.

The plant-protection formulation can in addition be a concentrated plant-protection formulation comprising:
a) a plant-protection active product,
b) the solvent,
c) optionally at least one emulsifying agent, preferably a surfactant, and
d) optionally water.

Plant-Protection Active Product a)

Plant-protection active products, in particular water-insoluble and solid products, are known to a person skilled in the art. The plant-protection active product can in particular be a herbicide, an insecticide, an acaricide, a fungicide or a rodenticide, for example a raticide.

Mention may be made, as nonlimiting examples of suitable active materials, inter alia, of ametryn, diuron, linuron, chlortoluron, isoproturon, metamitron, diazinon, aclonifen, atrazine, chlorothalonil, bromoxynil, bromoxynil heptanoate, bromoxynil octanoate, mancozeb, maneb, zineb, phenmedipham, propanil, the phenoxyphenoxy series, the heteroaryloxyphenoxy series, CMPP, MCPA, 2,4-D, simazine, the active products of the imidazolinone series, the family of the organophosphorus compounds, with in particular azinphos-ethyl, azinphos-methyl, alachlor, chlorpyrifos, diclofop-methyl, fenoxaprop-P-ethyl, methoxychlor, cypermethrin, fenoxycarb, cymoxanil, chlorothalonil, the neonicotinoid insecticides, the family of the triazole fungicides, such as azaconazole, bromuconazole, cyproconazole, difenoconazole, diniconazole, epoxiconazole, fenbuconazole, flusilazole, myclobutanil, tebuconazole, triadimefon and triadimenol, strobilurins, such as pyraclostrobin, picoxystrobin, azoxystrobin, famoxadone, kresoxim-methyl and trifloxystrobin, or sulfonylureas, such as bensulfuron-methyl, chlorimuron-ethyl, chlorsulfuron, metsulfuron-methyl, nicosulfuron, sulfometuron-methyl, triasulfuron and tribenuron-methyl.

The water-insoluble products are chosen from this list.

The plant-protection active product can be chosen in particular from azoles, preferably triazoles, preferably tebuconazole. Tebuconazole is the usual name of a compound known to a person skilled in the art, the formula of which is as follows:

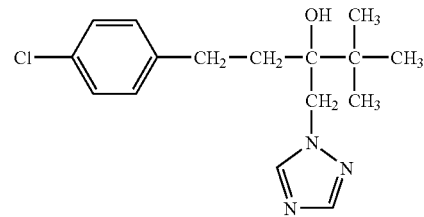 [SMILES: CC(C)(C)C(O)(CCc1ccc(Cl)cc1)Cn1cncn1]

Tebuconazole is a solid plant-protection product.

Mention may in particular be made, as triazoles other than tebuconazole, of the following compounds: azaconazole, bitertanol, bromuconazole, cyproconazole, diclobutrazole, difenoconazole, diniconazole, diniconazole-M, epoxiconazole, etaconazole, fenbuconazole, fluotrimazole, fluquinconazole, flusilazole, flutriafol, furconazole, furconazole-cis, hexaconazole, imibenconazole, ipconazole, metconazole, myclobutanil, penconazole, prochloraz, propiconazole, prothioconazole, quinconazole, strobilurin and analogs, simeconazole, tetraconazole, triadimefon, triadimenol, triazbutil, triflumizole, triticonazole, uniconazole or uniconazole-P.

The plant-protection active product can be chosen in particular from dinitroanilines, such as pendimethalin or trifluralin.

Use may in particular be made of the following plant-protection active products:

Alachlor

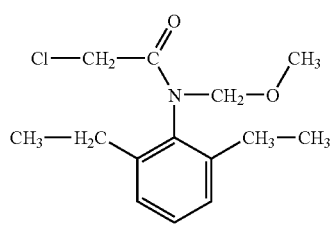 [SMILES: CCc1cccc(CC)c1N(COC)C(=O)CCl]

-continued
Chlorpyrifos
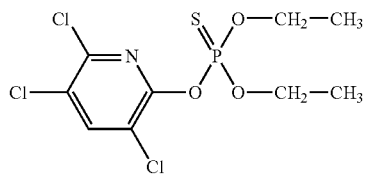 [SMILES: CCOP(=S)(OCC)Oc1nc(Cl)c(Cl)cc1Cl]
Alpha-cypermethrin
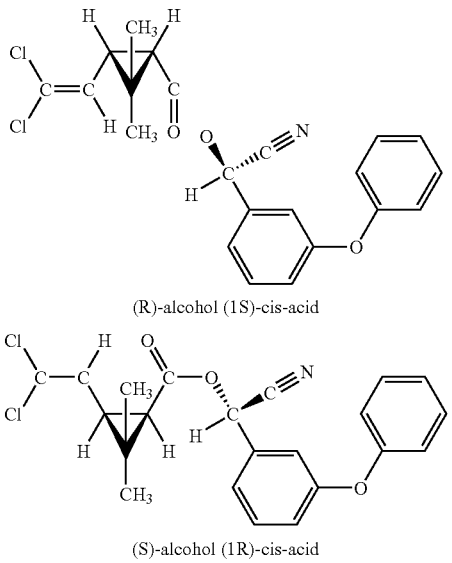
(R)-alcohol (1S)-cis-acid
(S)-alcohol (1R)-cis-acid
As racemic mixture and/or as isolated stereoisomers.
Phenmedipham
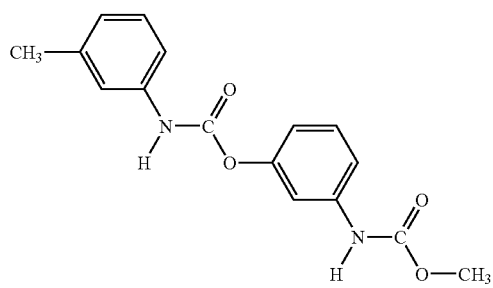
Propanil
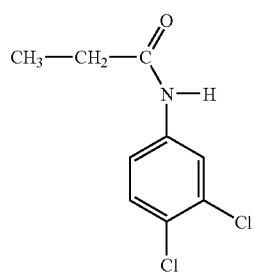
Pendimethalin
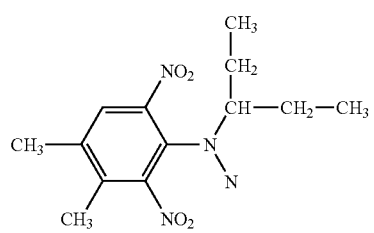 [SMILES: CCC(CC)N(N)c1c([N+](=O)[O-])cc(C)c(C)c1[N+](=O)[O-]]

-continued
Triadimenol 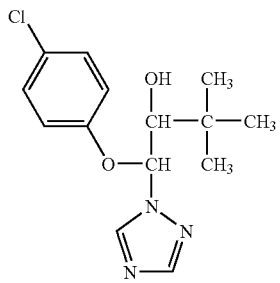 [SMILES: CC(C)(C)C(O)C(Oc1ccc(Cl)cc1)n1cncn1]
Trifluralin 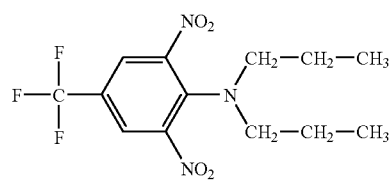 [SMILES: CCCN(CCC)c1c([N+](=O)[O-])cc(C(F)(F)F)cc1[N+](=O)[O-]]
Oxyfluorfen 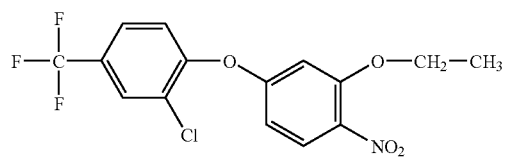
Dimethoate 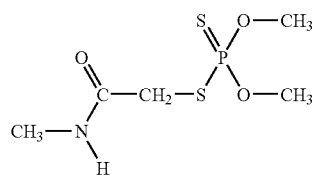
Imidacloprid 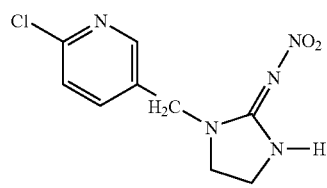 [SMILES: O=[N+]([O-])/N=C1\NCCN1Cc1ccc(Cl)nc1]
Propoxur 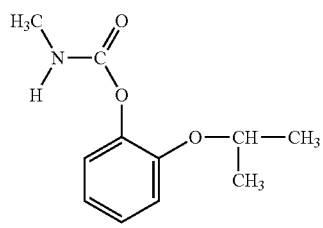
Benomyl 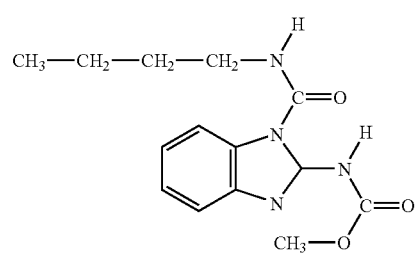 [SMILES: CCCCNC(=O)N1c2ccccc2NC1NC(=O)OC]

Deltamethrin
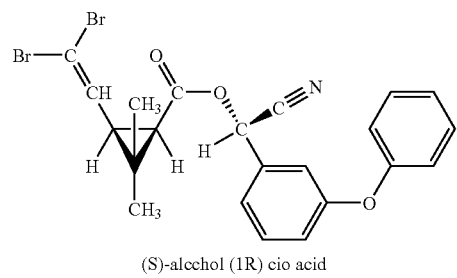 [SMILES: CC1(C)[C@H](C(=O)O[C@H](C#N)c2cccc(Oc3ccccc3)c2)[C@@H]1C=C(Br)Br]
(S)-alcohol (1R) cio acid
Fenvalerate
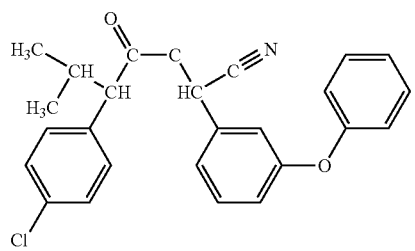 [SMILES: CC(C)C(C(=O)CC(C#N)c1cccc(Oc2ccccc2)c1)c1ccc(Cl)cc1]
Abamectin
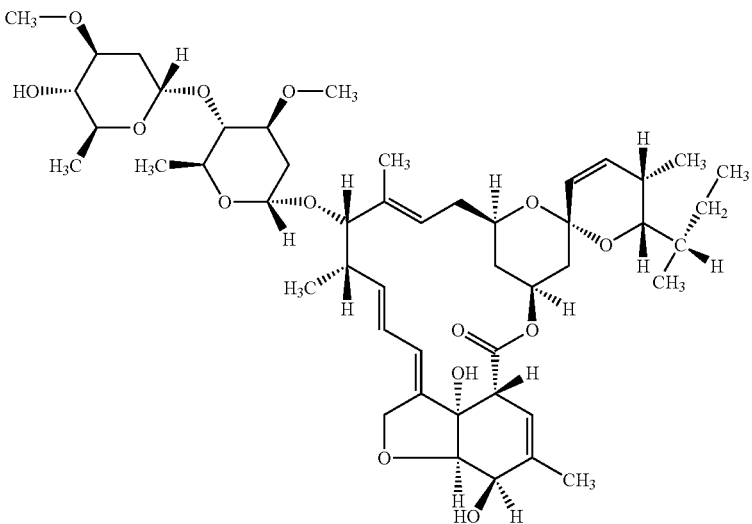
avermectin B$_{1a}$
(major component)
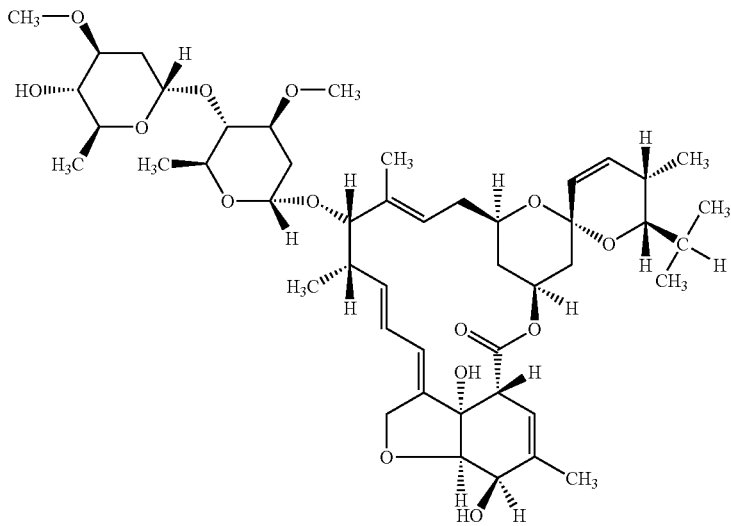
avermectin B$_{1b}$
(minor component)

-continued
Amicarbazone
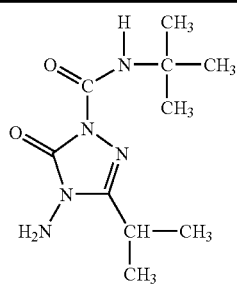
Bifenthrin
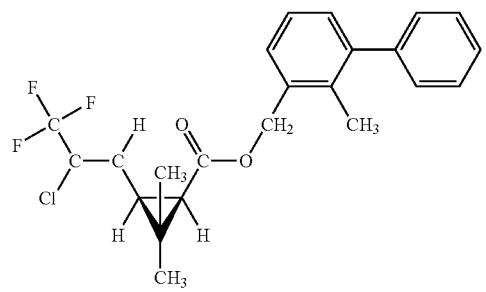
(Z)-(1R)-cis-acid
(Z)-(1S)-cis-acid
Carbosulfan
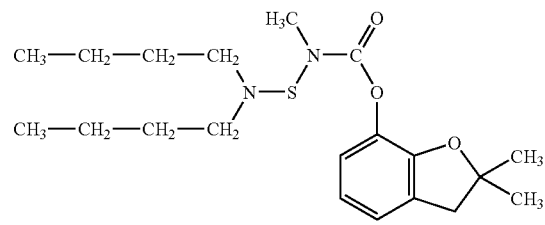 [SMILES: CCCCN(CCCC)SN(C)C(=O)Oc1cccc2c1OC(C)(C)C2]
Cyfluthrin
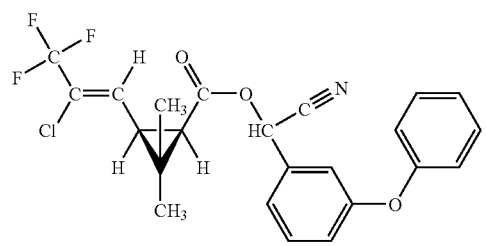
(Z)-(1R)-cis-acid
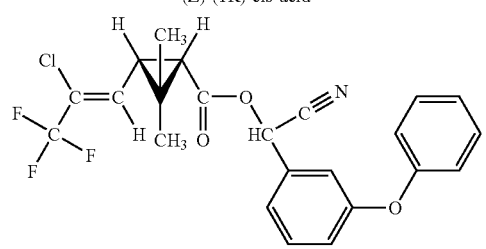
(Z)-(1S)-cis-acid -continued
Difenoconazole 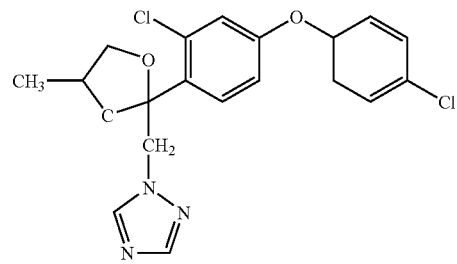 [SMILES: CC1COC(Cn2cncn2)(c2ccc(OC3C=CC(Cl)=CC3)cc2Cl)C1]
Etofenprox 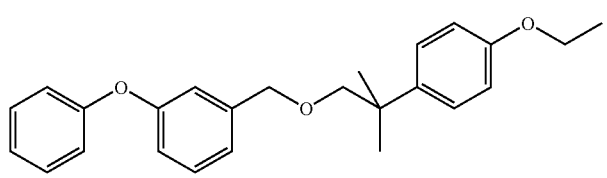 [SMILES: CCOc1ccc(C(C)(C)COCc2cccc(Oc3ccccc3)c2)cc1]
Fenoxaprop-ethyl 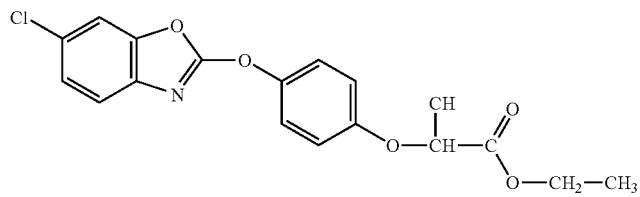 [SMILES: CCOC(=O)C(C)Oc1ccc(Oc2nc3ccc(Cl)cc3o2)cc1]
Fipronil 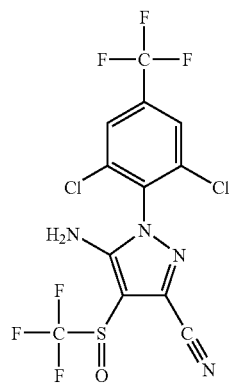 [SMILES: N#Cc1nn(-c2c(Cl)cc(C(F)(F)F)cc2Cl)c(N)c1S(=O)C(F)(F)F]
Fenvalerate 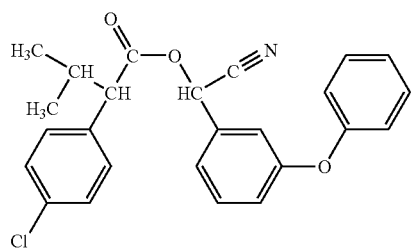
Fluazifop-P-butyl 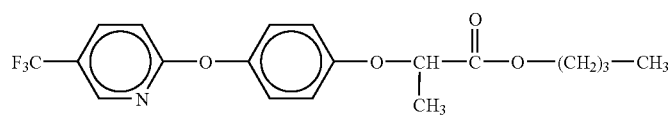

-continued
Flufenoxuron
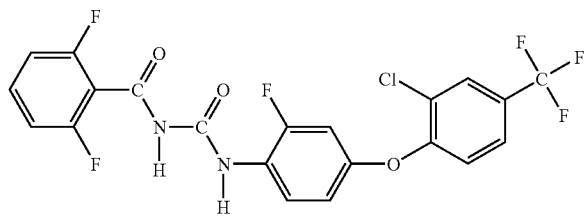 [SMILES: O=C(NC(=O)c1c(F)cccc1F)Nc1ccc(Oc2ccc(C(F)(F)F)cc2Cl)cc1F]
Hexazinone
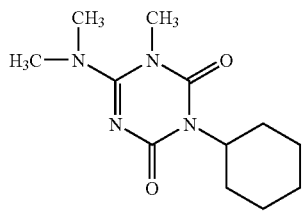 [SMILES: CN(C)c1nc(=O)n(C2CCCCC2)c(=O)n1C]
Lambda-
cyhalothrin
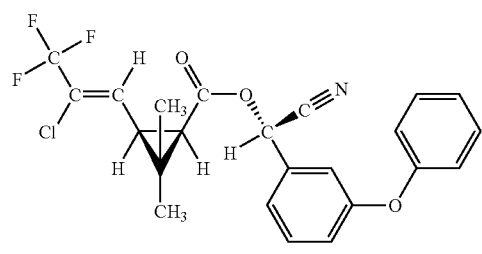
(S)-alcohol (Z)-(1R)-cis-acid
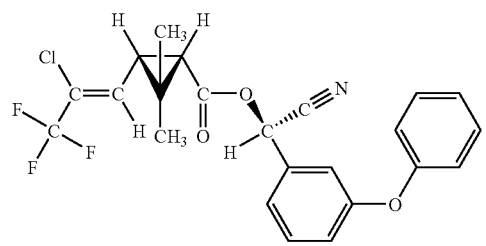
(R)-alcohol (Z)-(1S)-cis-acid
Methomyl
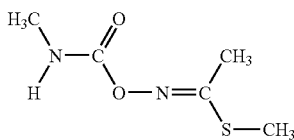
Permethrin
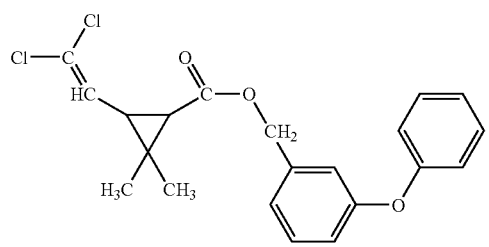 [SMILES: CC1(C)C(C=C(Cl)Cl)C1C(=O)OCc1cccc(Oc2ccccc2)c1]

-continued

Prochloraz

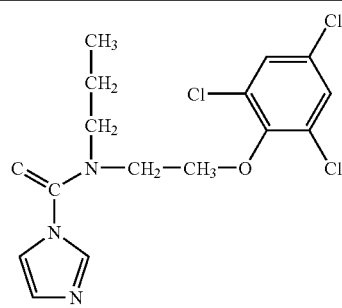

Propiconazole

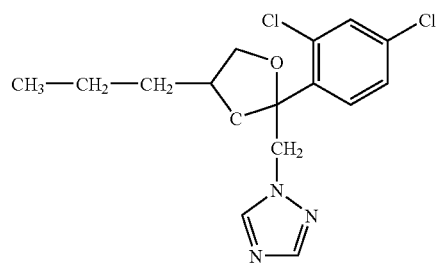 [SMILES: CCCC1COC(Cn2cncn2)(c2ccc(Cl)cc2Cl)C1]

Tebuconazole

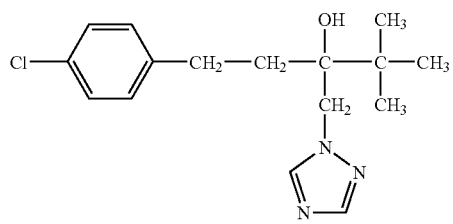 [SMILES: CC(C)(C)C(O)(CCc1ccc(Cl)cc1)Cn1cncn1]

These products and names are known to a person skilled in the art. It is possible to combine several plant-protection active products.

Emulsifying Agent c)

The plant-protection formulation can comprise an emulsifying agent, typically and preferably a surfactant. The emulsifying agents are agents intended to facilitate the emulsification or the dispersion, after bringing the formulation into contact with water, and/or to stabilize (over time and/or with regard to the temperature) the emulsion or the dispersion, for example by preventing sedimentation.

The surfactants are known compounds which exhibit a molar mass which is generally relatively low, for example less than 1000 g/mol. The surfactant can be an anionic surfactant, in the salified or acid form, a nonionic surfactant, preferably a polyalkoxylated surfactant, a cationic surfactant or an amphoteric surfactant (term also including zwitterionic surfactants). A mixture or a combination of these surfactants may be involved.

Mention may be made, as examples of anionic surfactants, without the intention to be limited thereto, of:

alkylsulfonic acids or arylsulfonic acids, optionally substituted by one or more hydrocarbon groups, the acid functional group of which is partially or completely salified, such as $C_8$-$C_{50}$, more particularly $C_8$-$C_{30}$ and preferably $C_{10}$-$C_{22}$ alkylsulfonic acids, benzenesulfonic acids or naphthalenesulfonic acids substituted by one to three $C_1$-$C_{30}$, preferably $C_4$-$C_{16}$, alkyl groups and/or $C_2$-$C_{30}$, preferably $C_4$-$C_{16}$, alkenyl groups.

mono- or diesters of alkyl sulfosuccinic acids, the linear or branched alkyl part of which, optionally substituted by one or more hydroxyl and/or linear or branched $C_2$-$C_4$ alkoxyl (preferably ethoxyl, propoxyl or ethopropoxyl) groups.

phosphate esters more particularly chosen from those comprising at least one saturated, unsaturated or aromatic and linear or branched hydrocarbon group comprising from 8 to 40, preferably from 10 to 30, carbon atoms, optionally substituted by at least one alkoxyl (ethoxyl, propoxyl or ethopropoxyl) group. In addition, they comprise at least one mono- or diesterified phosphate ester group, so that it is possible to have one or two free or partially or completely salified acid groups. The preferred phosphate esters are of the type of the mono- and diesters of phosphoric acid and of alkoxylated (ethoxylated and/or propoxylated) mono-, di- or tristyrylphenol or of alkoxylated (ethoxylated and/or propoxylated) mono-, di- or trialkylphenol, optionally substituted by one to four alkyl groups; of phosphoric acid and of an alkoxylated (ethoxylated or ethopropoxylated) $C_8$-$C_{30}$, preferably $C_{10}$-$C_{22}$, alcohol; or of phosphoric acid and of a nonalkoxylated $C_8$-$C_{22}$, preferably $C_{10}$-$C_{22}$, alcohol.

sulfate esters obtained from saturated or aromatic alcohols optionally substituted by one or more alkoxyl (ethoxyl, propoxyl or ethopropoxyl) groups and for which the sulfate functional groups exist in the free or partially or completely neutralized acid form. Mention may be made, by way of example, of the sulfate esters more particularly obtained from saturated or unsaturated $C_8$-$C_{20}$ alcohols which can comprise from 1 to alkoxyl (ethoxyl, propoxyl or ethopropoxyl) units; the sulfate esters obtained from polyalkoxylated phenol substituted by 1 to 3 saturated or unsaturated $C_2$-$C_{30}$ hydrocarbon groups and in which the number of alkoxyl units is between 2 and 40; or the sulfate esters obtained from polyalkoxylated mono-, di- or tristyrylphenol in which the number of alkoxyl units varies from 2 to 40.

The anionic surfactants can be in the acid form (they are potentially anionic) or in a partially or completely salified form, with a counterion. The counterion can be an alkali metal, such as sodium or potassium, an alkaline earth metal, such as calcium, or also an ammonium ion of formula $N(R)_4^+$ in which R, which are identical or different, represent a hydrogen atom or a $C_1$-$C_4$ alkyl radical optionally substituted by an oxygen atom.

Mention may be made, as examples of nonionic surfactants, without the intention to be limited thereto, of:

polyalkoxylated (ethoxylated, propoxylated or ethopropoxylated) phenols substituted by at least one $C_4$-$C_{20}$, preferably $C_4$-$C_{12}$, alkyl radical or substituted by at least one alkylaryl radical, the alkyl part of which is a $C_1$-$C_6$ alkyl part. More particularly, the total number of alkoxyl units is between 2 and 100. Mention may be made, by way of example, of polyalkoxylated mono-, di- or tri(phenylethyl)phenols or polyalkoxylated nonylphenols. Mention may be made, among ethoxylated and/or propoxylated, sulfated and/or phosphated, di- or tristyrylphenols, of the ethoxylated di(1-phenylethyl)phenol comprising 10 oxyethylene units, the ethoxylated di(1-phenylethyl)phenol comprising 7 oxyethylene units, the ethoxylated and sulfated di(1-phenylethyl) phenol comprising 7 oxyethylene units, the ethoxylated tri(1-phenylethyl)phenol comprising 8 oxyethylene units, the ethoxylated tri(1-phenylethyl)phenol comprising 16 oxyethylene units, the ethoxylated and sulfated tri(1-phenylethyl)phenol comprising 16 oxyethylene units, the ethoxylated tri(1-phenylethyl)phenol comprising 20 oxyethylene units or the ethoxylated and phosphated tri(1-phenylethyl)phenol comprising 16 oxyethylene units.

polyalkoxylated (ethoxylated, propoxylated or ethopropoxylated) $C_6$-$C_{22}$ fatty alcohols or acids. The number of the alkoxyl units is between 1 and 60. The term "ethoxylated fatty acid" includes both the products obtained by ethoxylation of a fatty acid with ethylene oxide and those obtained by esterification of a fatty acid with a polyethylene glycol.

polyalkoxylated (ethoxylated, propoxylated or ethopropoxylated) triglycerides of vegetable or animal origin. The triglycerides resulting from lard, tallow, groundnut oil, butter oil, cottonseed oil, linseed oil, olive oil, palm oil, grape seed oil, fish oil, soybean oil, castor oil, rapeseed oil, copra oil or coconut oil and comprising a total number of alkoxyl units of between 1 and 60 are thus suitable. The term "ethoxylated triglyceride" is targeted both at the products obtained by ethoxylation of a triglyceride with ethylene oxide and at those obtained by transesterification of a triglyceride with a polyethylene glycol.

optionally polyalkoxylated (ethoxylated, propoxylated or ethopropoxylated) sorbitan esters, more particularly cyclized sorbitol esters of $C_{10}$ to $C_{20}$ fatty acids, such as lauric acid, stearic acid or oleic acid, comprising a total number of alkoxyl units of between 2 and 50.

Emulsifiers of use are in particular the following products, all sold by Rhodia:

Soprophor TSP/724: surfactant based on ethopropoxylated tristyrylphenol

Soprophor 796/O: surfactant based on ethopropoxylated tristyrylphenol

Soprophor CY 8: surfactant based on ethoxylated tristyrylphenol

Soprophor BSU: surfactant based on ethoxylated tristyrylphenol

Alkamuls RC: surfactant based on ethoxylated castor oil

Alkamuls OR/36: surfactant based on ethoxylated castor oil

Alkamuls T/20: surfactant based on a sorbitan ester

The formulation advantageously comprises at least 4%, preferably at least 5%, preferably at least 8%, by weight of dry matter, of at least one surfactant c).

It is mentioned that the solvent can be combined with an aromatic and/or nonaromatic surfactant.

Other Details with Regard to the Plant-Protection Formulation

The concentrated plant-protection formulation does not comprise large amounts of water. Typically, the water content is less than 50% by weight, advantageously less than 25% by weight. It will generally be less than 10% by weight.

The formulation is preferably a liquid formulation, for example in the form of an emulsifiable concentrate (EC), a concentrated emulsion (EW) or a microemulsion (ME). In this case, it preferably comprises less than 500 g/l of water, more preferably less than 250 g/l. It will generally be less than 100 g/l.

The formulations can advantageously comprise:

a) from 4 to 60%, preferably from 10 to 50%, of the plant-protection product, by weight of active material, b) from 10 to 92%, preferably from 20 to 80%, of the solvent, by weight, c) from 4 to 60%, preferably from 5 to 50%, preferably from 8 to 25%, by weight of dry matter, of an emulsifier, preferably of a surfactant, d) from 0 to 10% by weight of water.

The production of solid formulations, for example of formulations in which a liquid comprising the plant-protection product dissolved in the solvent is supported by a mineral and/or dispersed in a solid matrix, is not ruled out.

The formulation can, of course, comprise ingredients (or "additives") other than the plant-protection active product, the solvent(s), the optional emulsifying agent(s) and the optional water. It can in particular comprise viscosity-modifying agents, antifoaming agents, in particular silicone antifoaming agents, sticking agents, anti-leaching agents, inert fillers, in particular inorganic fillers, antifreeze agents, and the like.

The formulations can in particular comprise additives, referred to as "other additives", not participating in the definition of the products a), b) or c), such as:

other solvents, generally in a small amount, that is to say in an amount smaller than the amount of the solvents b1), b2) and b3), that is to say in a smaller amount than the solvent in the solvent system which is present in the smallest amount. An other solvent is not understood as forming part of the solvent system. Mention is in particular made, as other solvents, of the solvents of the family of the phosphates, phosphonates or phosphine oxides, such as TEBP, TBP, TEPO or DBBP. Mention is also made of alkyldimethylamides where the alkyl is a $C_6$-$C_{18}$ alkyl, in particular those sold under the Genagen brand. Mention is also made of ester lactates, in particular those sold under the Purasolv brand. Mention is also made of methyl esters of fatty acids, in particular those sold under the Phytorobe brand. Mention is also made of diacid diesters ("DiBasic Esters"), in particular those sold by Rhodia under the Rhodiasolv RPDE and Rhodiasolv DIB brands. Mention is also made of hydrocarbon fractions, cyclic amides and lactones.

crystallization inhibitors. They can be the solvents mentioned above. They can also be nonpolyalkoxylated fatty acids or fatty alcohols. Mention is made, for example, of the product Alkamuls OL700.

Conventional processes for the preparation of plant-protection formulations or mixtures of solvents can be employed. It is possible to carry out simple mixing of the constituents.

The concentrated plant-protection formulation is intended to be spread over a cultivated field or a field to be cultivated, for example of soya, generally after diluting in water, in order to obtain a dilute composition. Diluting is generally carried out by the farmer, directly in a tank (tank-mix), for example in the tank of a device intended to spread the composition. The addition by the farmer of other plant-protection products, for example fungicides, herbicides, pesticides or insecticides, or fertilizers is not ruled out. Thus, the formulation can be used to prepare a dilute composition in water of the plant-protection active product by mixing at least one part by weight of concentrated formulation with at least 10 parts by weight of water, preferably less than 1000 parts by weight of water. The degrees of dilution and the amounts to be applied to the field generally depend on the plant-protection product and on the dose desirable for treating the field; this can be determined by the farmer.

Other details or advantages may become apparent in the light of the examples which follow, without implied limitation.

EXAMPLES

Example 1

Preparation of a material composition comprising 80-90% by weight of N,N,N,N-tetramethyl-2-methylglutaramide of following formula

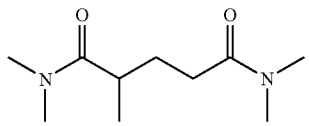

Stage 1, Preliminary: Preparation of the Mixture of Acids

Starting material: "MGN": mixture of dinitriles with the following composition by weight:

| | |
|---|---|
| Methylglutaronitrile (MGN): | 84.2% |
| Ethylsuccinonitrile (ESN): | 11% |
| Adiponitrile (AdN): | 4% |

The remainder to 100% corresponds to various impurities not comprising nitrile functional groups.

The MGN (10.8 g, 0.1 mol) is mixed with a 25% by weight aqueous KOH solution (134 g) at reflux for 19 hours. The resulting medium is homogeneous. It is washed with t-BuOMe (100 ml), then cooled to 0° C. and then acidified with 50 ml of a 37% aqueous HCl solution (pH 2). The diacid obtained is extracted with ethyl acetate (3 times 50 ml). The organic phases are combined and dried over MgSO$_4$, filtered and evaporated. 14.4 g of solid product are obtained (melting point 76-78° C.)

Stage 2: Conversion to Amides 750 ml of toluene and triethylamine (260 ml, 4.47 mol) are charged to a 3000 ml round-bottomed three-necked flask under a nitrogen atmosphere and cooling is carried out at −5° C. using a bath of ice and NaCl. Diethylamine (500 ml, 7.542 mol, 2.1 equivalents) is first added at this temperature and then 329 g of a mixture of 2-methylglutaric acid (84.6% by weight of the mixture), 2-ethylsuccinic acid (11% by weight of the mixture) and adipic acid (4.1% by weight of the mixture) in solution in 750 ml of toluene are added dropwise over one hour. Once the addition is complete, the mixture is diluted using 300 ml of toluene and the medium is allowed to warm to ambient temperature and mixed for 12 hours. Subsequently, the salt is filtered off and washed with ethyl acetate. The organic solutions (resulting from the filtration and the washing) are combined and concentrated under reduced pressure to produce 378 g of crude product (yellow oil). Distillation is carried out (120° C.-140° C., 15 Pa) and 352 g of a yellow oil are obtained, which oil comprises (analysis by gas chromatography) 86.3% by weight of N,N,N,N-tetramethyl-2-methylglutaramide, 2.2% by weight of N,N,N,N-tetramethyladipamide and 6.7% by weight of N,N,N,N-tetramethyl-2-methylglutaramide.

The yield is 92%.

Example 2

Preparation of a material composition comprising more than 98% by weight of N,N,N,N-tetramethyl-2-methylglutaramide of following formula

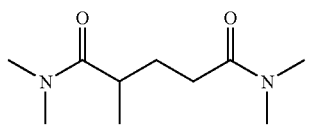

A mixture of 2-methylglutaric acid (15 g, 100 mmol) and 50 ml of thionyl chloride is heated at 60° C. for 5 hours. Subsequently, the excess thionyl chloride is removed by evaporation under vacuum. The residual liquid is diluted in 100 ml of anhydrous toluene and then the resulting solution is introduced dropwise over 45 minutes into a three-necked reactor comprising triethylamine (28.3 ml, 200 mmol) and dimethylamine (20 ml, 1.5 equivalents) at approximately 0° C. The medium is subsequently allowed to warm to ambient temperature and mixing is carried out for 6 hours. 50 ml of ethyl acetate are subsequently added; this results in a solid, which is filtered off and washed using 50 ml of ethyl acetate. The organic solutions (resulting from the filtration and the washing) are combined and concentrated to produce 20 g of crude product (yellow oil). The crude product is purified by distillation under vacuum to produce 13.63 g of N,N,N,N-tetramethyl-2-methylglutaramide. The purity is 98.3% and the yield is 67%.

Example 3

Preparation of a material composition comprising 80-90% by weight of N,N,N,N-tetraethyl-2-methylglutaramide of following formula

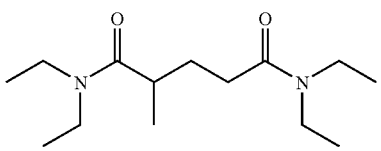 [SMILES: CCN(CC)C(=O)CCC(C)C(=O)N(CC)CC]

Starting material: "MGN": mixture of dinitriles with the following composition by weight:

| | |
|---|---|
| Methylglutaronitrile (MGN): | 84.2% |
| Ethylsuccinonitrile (ESN): | 11% |
| Adiponitrile (AdN): | 4% |

The remainder to 100% corresponds to various impurities not comprising nitrile functional groups.

Stage 1

The MGN (10.8 g, 0.1 mol) is mixed with a 25% by weight aqueous KOH solution (134 g) at reflux for 19 hours. The resulting medium is homogeneous. It is washed with t-BuOMe (100 ml), then cooled to 0° C. and then acidified with 50 ml of a 37% aqueous HCl solution (pH 2). The diacid obtained is extracted with ethyl acetate (3 times 50 ml). The organic phases are combined and dried over MgSO$_4$, filtered and evaporated. 14.4 g of solid product are obtained (melting point 76-78° C.)

Stage 2: Conversion to Amides 200 g of a mixture of 2-methylglutaric acid (84.6% by weight of the mixture), 2-ethylsuccinic acid (11% by weight of the mixture) and adipic acid (4.1% by weight of the mixture) and 650 ml of thionyl chloride are heated as a mixture at 60° C. for 5 hours. Subsequently, the excess thionyl chloride is removed by evaporation under a slight vacuum. The residual liquid is diluted in 500 ml of anhydrous toluene and then the resulting solution is introduced dropwise over 60 minutes into a three-necked reactor comprising 500 ml of anhydrous toluene, 425 ml of dimethylamine and 400 ml of triethylamine at approximately 5° C. Mixing is carried out for 12 hours in order to carry out the reaction. 1 l of ethyl acetate is subsequently added and the salt is filtered off and washed using 800 ml of ethyl acetate. The filtrate is partially concentrated to 500 ml and then washed with 1 l of a saturated NaHCO$_3$ solution. After separation by settling, the aqueous layer is extracted with 500 ml of ethyl acetate. The organic phases are combined and concentrated to produce 279 g of crude product. Distillation is carried out at 140° C. under high vacuum and 205 g of final product are obtained, which product is a mixture mainly comprising (analysis by gas chromatography) 85.3% by weight of N,N,N,N-tetraethyl-2-methylglutaramide, 2.25% by weight of N,N,N,N-tetraethyladipamide and 5.99% by weight of N,N,N,N-tetraethyl-2-ethylsuccinamide.

Example 4

Preparation of a material composition comprising more than 98% by weight of N,N,N,N-tetraethyl-2-methylglutaramide of following formula

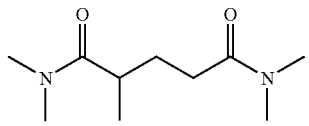

A mixture of 2-methylglutaric acid (80 g, 0.542 mol) and 260 ml of thionyl chloride (424 g, 3.56 mol) is heated at 60° C. for 5 hours. Subsequently, the excess thionyl chloride is removed by evaporation under vacuum. The residual liquid is diluted in 200 ml of anhydrous toluene and then the resulting solution is introduced dropwise over 60 minutes into a three-necked reactor comprising 200 ml of toluene, triethylamine (160 ml, 116.2 g, 1.14 mol) and diethylamine (170 ml, 115.6 g, 1.58 mol) at approximately 0° C. The medium is subsequently allowed to warm to ambient temperature and mixing is carried out for 6 hours. After the end of the reaction (monitored by HPLC analysis), 500 ml of ethyl acetate are added; this results in a solid, which is filtered off and washed using 250 ml of ethyl acetate. The filtrate is concentrated to 500 ml and then washed with 500 ml of a 0.2M aqueous NaOH solution. After separation by settling, the aqueous phase is washed using 250 ml of ethyl acetate. The organic phases (resulting from the filtration and the washing) are combined and concentrated to produce 110 g of crude product. Distillation is carried out at 158° C. under a pressure of 3 mbar to produce 93.5 g of N,N,N,N-tetraethyl-2-methylglutaramide. The purity is 98.2% and the yield is 66%.

Example 5

Preparation of a material composition comprising 80-95% by weight of N,N,N,N-tetra(n-propyl)-2-methylglutaramide

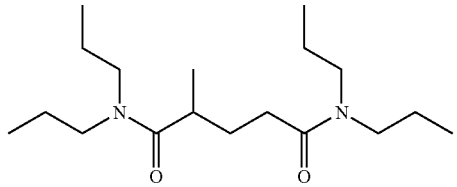 [SMILES: CCCN(CCC)C(=O)CCC(C)C(=O)N(CCC)CCC]

Starting material: "MGN": mixture of dinitriles with the following composition by weight:

| | |
|---|---|
| Methylglutaronitrile (MGN): | 84.2% |
| Ethylsuccinonitrile (ESN): | 11% |
| Adiponitrile (AdN): | 4% |

The remainder to 100% corresponds to various impurities not comprising nitrile functional groups.

Stage 1

A mixture of diacids comprising 2-methylglutaric acid (84.6% by weight of the mixture), 2-ethylsuccinic acid (11% by weight of the mixture) and adipic acid (4.1% by weight of the mixture) is prepared as indicated for stage 1 of example 3.

Stage 2

The devolatilized mixture of diacids (600 g, 4.106 mol) is mixed with 1210 ml of thionyl chloride (1973.5 g, 16.423 mol) and heated at 60° C. for 4 hours. Subsequently, the excess thionyl chloride is removed by evaporation under vacuum to produce 1446 g of crude product. After distillation (86/87° C., 350 Pa), 1256 g of dichloride are obtained (yield of 83.6% for this first stage). This stage is repeated a second time.

The dichloride (850 g, 4.644 mol) is diluted in 500 ml of anhydrous toluene and then the resulting solution is introduced dropwise over 180 minutes into a three-necked reactor comprising 4000 ml of toluene, triethylamine (1175 ml, 853.1 g, 11.610 mol) and diethylamine (1780 ml, 1317.2 g, 13.017 mol) at approximately 0-10° C. The medium is subsequently allowed to warm to ambient temperature and mixing is carried out for 4 hours. The medium is filtered and the solid is washed with ethyl acetate. The filtrates are combined and evaporated under vacuum. 2000 ml of saturated $NaHCO_3$ solution are added to the residue. The mixture obtained is separated and the aqueous phase with ethyl acetate (1000 ml×6). The organic phases are combined, dried over sodium sulfate and then evaporated under vacuum. 1150 g of final product are obtained after distillation under vacuum (the yield is 78.6%, with respect to the dichloride).

Examples 6 to 10

Plant-Protection Formulations

Formulations of various plant-protection active principles of emulsifiable concentrate (EC) type are prepared by mixing the ingredients.

The formulations comprise:
the active principle, in the amount by weight (of active material) shown in the table below,
10% by weight of Alkamuls RC surfactant,
and, as solvent, the balance of compound or material composition of the examples.

Examples 11.1 to 11.3 are comparative examples, where use is made, as solvent, of Rhodiasolv ADMA10 from Rhodia (Asia Pacific region): alkyldimethylamide solvent.

The following tests are carried out:
visual observation at 25° C.—the appearance of the formulation is recorded and possibly the presence of crystals is detected
visual observation at 0° C.—the formulation is placed at 0° C. for 7 days and the appearance of the formulation is recorded and possibly the presence of crystals is detected (CIPAC MT39 test)
visual observation at 0° C. with nucleation: a crystal of the active material is introduced into the formulation which has spent 7 days at 0° C., for nucleation, and the formulation is again placed at 0° C. for 7 days. The appearance of the formulation is recorded and possibly the presence of crystals is detected.

| Example | Solvent | Active principle | Appearance at 25° C. | Appearance at 0° C. | Appearance at 0° C. with nucleation |
|---|---|---|---|---|---|
| 6.1 | Example 1 | Chlorpyrifos - 40% | Clear | Clear | / |
| 6.2 | Example 1 | Fastac - 10% | Clear | Clear | Clear |
| 6.3 | Example 1 | Propanil - 36% | Clear | Clear | Clear |
| 6.4 | Example 1 | Tebuconazole - 25% | Clear | Clear | Clear |
| 6.5 | Example 1 | Oxyfluorfen - 22% | Clear | Clear | Clear |
| 7.1 | Example 2 | Phenmedipham - 16% | Clear | Clear | Clear |
| 7.2 | Example 2 | Propanil - 36% | Clear | Clear | Clear |
| 7.3 | Example 2 | Tebuconazole - 25% | Clear | Clear | Clear |
| 7.4 | Example 2 | Oxyfluorfen - 22% | Clear | Clear | Clear |
| 7.5 | Example 2 | Propoxur - 20% | Clear | Clear | Clear |
| 8.1 | Example 3 | Tebuconazole - 25% | Clear | Clear | Clear |
| 8.2 | Example 3 | Propoxur - 20% | Clear | Clear | Clear |
| 9.1 | Example 4 | Phenmedipham - 16% | Clear | Clear | Clear |
| 9.2 | Example 4 | Propanil - 36% | Clear | Clear | Clear |
| 9.3 | Example 4 | Tebuconazole - 25% | Clear | Clear | Clear |
| 9.4 | Example 4 | Oxyfluorfen - 22% | Clear | Clear | Clear |
| 9.5 | Example 4 | Propoxur - 20% | Clear | Clear | Clear |
| 10.1 | Example 5 | Pendimethalin - 33% | Clear | Clear | / |
| 10.2 | Example 5 | Triadimenol - 23% | Clear | Clear | Clear |
| 11.1C | Rhodiasolv ® ADMA 10 (comp.) | Oxyfluorfen - 22% | Clear | Clear | Crystals |
| 11.2C | Rhodiasolv ® ADMA 10 (comp.) | Pendimethalin - 33% | Clear | Crystals | Crystals |
| 11.3C | Rhodiasolv ® ADMA 10 (comp.) | Triadimenol - 23% | Clear | Clear | Crystals |

What is claimed is:

1. A composition comprising at least 10% by weight of a bis(dialkylamide) compound of the formula:

$$R^2R^3NOC-R^{1a}-CONR^4R^5 \quad (Ia)$$

wherein:
$R^2$, $R^3$, $R^4$ and $R^5$, which are identical or different, are each a linear or branched or cyclic $C_1$-$C_6$ alkyl radical or a phenyl radical, and
$R^{1a}$ is a divalent group of the formula:

$$-CH_2-CH_2-(CHR^6)_x-$$

wherein:
x is an integer greater than 0, and
$R^6$ is a $C_1$-$C_6$ alkyl group, wherein said composition is formulated as a plant protection formulation, a cleaning formulation, a stripping formulation, a degreasing formulation, a lubricating or textile formulation, a coating formulation, a pigment or ink formulation or a plastic formulation.

2. The composition as defined by claim 1, comprising an amidation or transamidation product.

3. The composition as defined by claim 1, further comprising a compound having the following formula (Ib):

$$R^2R^3NOC-R^{1b}-CONR^4R^5 \quad (Ib)$$

wherein:
R$^2$, R$^3$, R$^4$ and R$^5$, which may be identical or different, are each a linear or branched or cyclic C$_1$-C$_6$ alkyl radical or a phenyl radical, and
R$^{1b}$ is a divalent radical of formula (IIb):

$$-CH_2-(CHR^7)_z-(CHR^6)_x-(CHR^7)_y- \quad (IIb)$$

wherein:
x is an integer greater than 0,
y is a mean integer greater than or equal to 0,
z is a mean integer greater than or equal to 0,
R$^6$ is a C$_1$-C$_6$ alkyl radical, and
R$^7$ is a hydrogen atom or a C$_1$-C$_6$ alkyl radical.

4. The composition as defined by claim 3, wherein, in the R$^{1b}$ radical:
x = 1,
y = z = 0,
R$^6$ = ethyl.

5. The composition as defined by claim 1, comprising a product of the amidation or transamidation of a mixture of methylglutaric acid and ethylsuccinic acid, or of a diester of this mixture.

6. The composition as defined by claim 3, which comprises:
from 70% to 95% by weight of the compound of formula (Ia),
from 5% to 30% by weight of a compound of formula (Ib), and
optionally, at most 15% by weight of another compound.

7. A process for the preparation of a bis(dialkylamide) compound of the formula:

$$R^2R^3NOC-R^{1a}-CONR^4R^5 \quad (Ia)$$

wherein:
R$^2$, R$^3$, R$^4$ and R$^5$, which are identical or different, are each a linear or branched or cyclic C$_1$-C$_6$ alkyl radical or a phenyl radical, and
R$^{1a}$ is a divalent group of the formula:

$$-CH_2-CH_2-(CHR^6)_x-$$

wherein:
x is an integer greater than 0, and
R$^6$ is a C$_1$-C$_6$ alkyl group,
said process comprising a stage of amidation or transamidation by a compound of formula R$^2$R$^3$NR and/or HNR$^4$R$^5$ of a compound of following formula (I'a):

$$R^8OOC-R^{1a}-COOR^8 \quad (I'a)$$

the compound of formula (I'a) optionally being in admixture with a compound of following formula (Ib):

$$R^8OOC-R^{1b}-COOR^8 \quad (I'b)$$

wherein:
R$^8$ is a hydrogen atom or a C$_1$-C$_6$ alkyl radical, and
R$^{1a}$ is a divalent radical of the formula:

$$-CH_2-CH_2-(CHR^6)_x-$$

wherein:
x is an integer greater than 0,
R$^6$ is a C$_1$-C$_6$ alkyl radical, and
R$^{1b}$ is a divalent radical of formula (IIb):

$$-CH_2-(CHR^7)_z-(CHR^6)_x-(CHR^7)_y- \quad (IIb)$$

wherein:
x is an integer greater than 0,
y is a mean integer greater than or equal to 0,
z is a mean integer greater than or equal to 0,
R$^6$ is a C$_1$-C$_6$ alkyl radical, and
R$^7$ is a hydrogen atom or a C$_1$-C$_6$ alkyl radical.

8. The composition of claim 1, wherein the bis(dialkylamide) compound in said composition is coalescence agent, a solvent, a cosolvent and/or a crystallization inhibitor.

9. The composition as defined by claim 1, wherein said composition comprises at least 50% by weight of said bis(dialkylamide) compound.

10. The composition as defined by claim 1, wherein, in formula (Ia), R$^2$, R$^3$, R$^4$ and R$^5$, which are identical or different, are selected from the group consisting of methyl, ethyl, n-propyl, isopropyl, n-butyl, isobutyl, n-pentyl, amyl, isoamyl, hexyl and cyclohexyl groups.

11. The composition as defined by claim 1, wherein, in the group R$^{1a}$:
x = 1,
y = z = 0, and
R$^6$ = methyl.

12. The composition as defined by claim 1, wherein, in formula (Ia), the R$^2$, R$^3$, R$^4$ and R$^5$ groups, which are identical or different, are linear C1-C4 alkyl groups.

13. A plant-protection formulation comprising an active plant protection agent, an emulsifier and at least one compound of the formula:

$$R^2R^3NOC-R^{1a}-CONR^4R^5 \quad (Ia)$$

wherein:
R$^2$, R$^3$, R$^4$ and R$^5$, which are identical or different, are each a linear or branched or cyclic C$_1$-C$_6$ alkyl radical or a phenyl radical, and R$^{1a}$ is a divalent group of the formula:

$$-CH_2-CH_2-(CHR^6)_x-$$

wherein:
x is an integer greater than 0, and
R$^6$ is a C$_1$—C$_6$ alkyl group,
wherein said plant-protection formulation is in the form of an emulsifiable concentrate, a concentrated emulsion, a microemulsion, a wettable-powder or a water-dispersible granule.

14. A composition comprising the plant-protection formulation of claim 13, wherein said plant-protection formulation is diluted with water.

* * * * *